(12) United States Patent
Yamauchi (10) Patent No.: US 7,408,644 B2
(45) Date of Patent: Aug. 5, 2008

(54) COLORATION MEASURING DEVICE

(75) Inventor: Kazunori Yamauchi, Hamamatsu (JP)

(73) Assignee: Hamamatsu Photonics K.K., Hamamatsu-shi, Shizuoka (JP)

( * ) Notice: Subject to any disclaimer, the term of this patent is extended or adjusted under 35 U.S.C. 154(b) by 359 days.

(21) Appl. No.: 10/535,259

(22) PCT Filed: Oct. 30, 2003

(86) PCT No.: PCT/JP03/13936

§ 371 (c)(1),
(2), (4) Date: May 18, 2005

(87) PCT Pub. No.: WO2004/046699

PCT Pub. Date: Jun. 3, 2004

(65) Prior Publication Data

US 2006/0055930 A1     Mar. 16, 2006

(30) Foreign Application Priority Data

Nov. 19, 2002   (JP) ............................. 2002-335641

(51) Int. Cl.
*G01J 3/46*   (2006.01)
(52) U.S. Cl. ...................................... 356/402
(58) Field of Classification Search ................. 356/402
See application file for complete search history.

(56) References Cited

U.S. PATENT DOCUMENTS

| | | | | |
|---|---|---|---|---|
| 4,676,653 A | * | 6/1987 | Strohmeier et al. | 356/446 |
| 4,833,088 A | * | 5/1989 | DeSimone et al. | 422/55 |
| 5,889,585 A | | 3/1999 | Markart | |
| 6,248,598 B1 | | 6/2001 | Bogema | |
| 7,070,920 B2 | * | 7/2006 | Spivey et al. | 356/246 |
| 2002/0097454 A1 | * | 7/2002 | Gudaitis | 358/509 |
| 2006/0176483 A1 | * | 8/2006 | Rudolf | 356/402 |

FOREIGN PATENT DOCUMENTS

| | | |
|---|---|---|
| EP | 0 183 524 | 6/1986 |
| EP | 0 286 101 | 10/1988 |
| EP | 0 994 343 | 4/2000 |
| JP | 63-269046 | 11/1988 |
| JP | 64-026160 | 1/1989 |
| JP | 7-151689 | 6/1995 |
| JP | 11-083745 | 3/1999 |
| JP | 11-237386 | 8/1999 |
| JP | 11-326191 | 11/1999 |
| JP | 2000-121443 | 4/2000 |

* cited by examiner

Primary Examiner—Kara E Geisel
(74) Attorney, Agent, or Firm—Drinker Biddle & Reath LLP

(57) ABSTRACT

A scanning mechanism 6 moves an optical head 5 relative to a mount plate 2 in a scan direction, and light emitting diodes 3A, 3B mounted on the optical head 5 emit their respective beams of measurement light along the scan direction and onto two color regions TP3, TP3, respectively, of an immunochromatographic test strip mounted on the mount plate 2. Photodiodes 4A, 4B mounted on the optical head 5 receive respective beams of reflected light from the two color regions TP3, TP3 perpendicularly to colored lines on the immunochromatographic test strip, thereby implementing simultaneous measurement of color intensities of the colored lines formed in the two color regions TP3, TP3 of the immunochromatographic test strip.

6 Claims, 6 Drawing Sheets

COLORATION MEASURING DEVICE

TECHNICAL FIELD

The present invention relates to a color measuring device for measuring a color intensity of a test strip such as an immunochromatographic test strip.

BACKGROUND ART

An immunochromatographic test strip has a color region preliminarily coated with a bandlike coating of an antibody (or antigen) which brings about an antigen-antibody reaction with an antigen (or antibody) in analyte. When the antigen (or antibody) in analyte labeled with a dye is developed to the color region of the test strip by a developing solution, the antigen (or antibody) in analyte undergoes the antigen-antibody reaction with the bandlike coating of the antibody (or antigen) to be trapped, thus forming a colored line of color caused by the dye in the color region.

With the immunochromatographic test strip of this type, the amount of the antigen (or antibody) in analyte can be quantitatively determined by optically measuring the color intensity of the colored line formed in the color region, by means of a measuring device.

As a device for measuring the color intensity of the test strip such as the immunochromatographic test strip, there is a conventionally well-known device configured to irradiate measurement light onto the colored line (color zone) formed in the color region of the test strip and to receive reflected light thereof to measure the color intensity of the colored line (e.g., reference is made to Patent Document 1 and Patent Document 2).

[Patent Document 1] Japanese Patent Application Laid-Open No. 11-326191

[Patent Document 2] Japanese Patent Application Laid-Open No. 11-83745

DISCLOSURE OF THE INVENTION

Incidentally, concerning the above-described immunochromatographic test strip, there are increasing demands for increase in the number of kinds of antigens (or antibodies) in analyte that can be analyzed by a single measurement. For meeting such demands, it is contemplated to expand the color region of the test strip to increase the number of kinds of antigens (or antibodies) in analyte to be trapped, and in this case, an appropriate configuration in view of the size of the test strip and handlability is such that at least two independent color regions are arranged in parallel to each other.

An object of the present invention is therefore to provide a color measuring device directed to a specific test strip in which at least two independent color regions are arranged in parallel to each other, and permitting simultaneous measurement of color intensities of colored lines formed in the respective color regions.

In order to achieve the above object, a color measuring device according to the present invention is a device for irradiating measurement light onto each colored line formed in a color region of a test strip and for receiving reflected light of the measurement light to measure a color intensity of each colored line, the device comprising: a single mount plate for mounting of a specific test strip in which at least two independent color regions are arranged in parallel to each other; a plurality of irradiation optical systems for irradiating respective beams of measurement light onto the associated color regions of the specific test strip; a plurality of reception optical systems for receiving respective beams of reflected light from the associated color regions; an optical head carrying the plurality of irradiation optical systems and reception optical systems; and a scanning mechanism for effecting relative movement between the mount plate and the optical head in a scan direction traversing each colored line.

In the color measuring device according to the present invention, the scanning mechanism effects the relative movement between the mount plate and the optical head in the scan direction traversing each colored line, the irradiation optical systems irradiate their respective beams of measurement light along the scan direction onto at least two color regions of the specific test strip mounted on the mount plate, and the reception optical systems receive their respective beams of reflected light from the associated color regions across each colored line, thereby simultaneously measuring color intensities of colored lines formed in at least two color regions of the specific test strip.

Preferably, the plurality of irradiation optical systems and the plurality of reception optical systems are optically isolated from each other. In this case, crosstalk is prevented between the plurality of reception optical systems, so as to improve the accuracy of measurement of color intensities for the plurality of color regions of the specific test strip.

Preferably, the plurality of irradiation optical systems and the plurality of reception optical systems are mounted on the single optical head. In this case, the structure is simple and only one system of the scanning mechanism suffices for movement of the optical head in the scan direction, thereby simplifying the structure of the scanning mechanism and a configuration of a control system thereof.

Preferably, the scanning mechanism is arranged to move the optical head relative to the mount plate in the scan direction. In this case, the specific test strip mounted on the mount plate is kept at rest without vibration, so as to improve the measurement accuracy of color intensities for at least two color regions of the specific test strip.

Preferably, the specific test strip is housed in a dedicated casing having a plurality of measurement windows for exposing at least two color regions, and a plurality of drop windows for dropwise delivery of a developing solution to effect development in each color region.

In the present specification, the specific test strip refers to at least two independent test plates provided with their respective development regions with a developing solution including color regions, or to a single test strip sectioned into at least two development regions including color regions.

BEST MODE FOR CARRYING OUT THE INVENTION

A color measuring device according to an embodiment of the present invention will be described with reference to the drawings. The same elements or elements with the same functionality will be denoted by the same reference symbols throughout the description, without redundant description.

Figure 1:
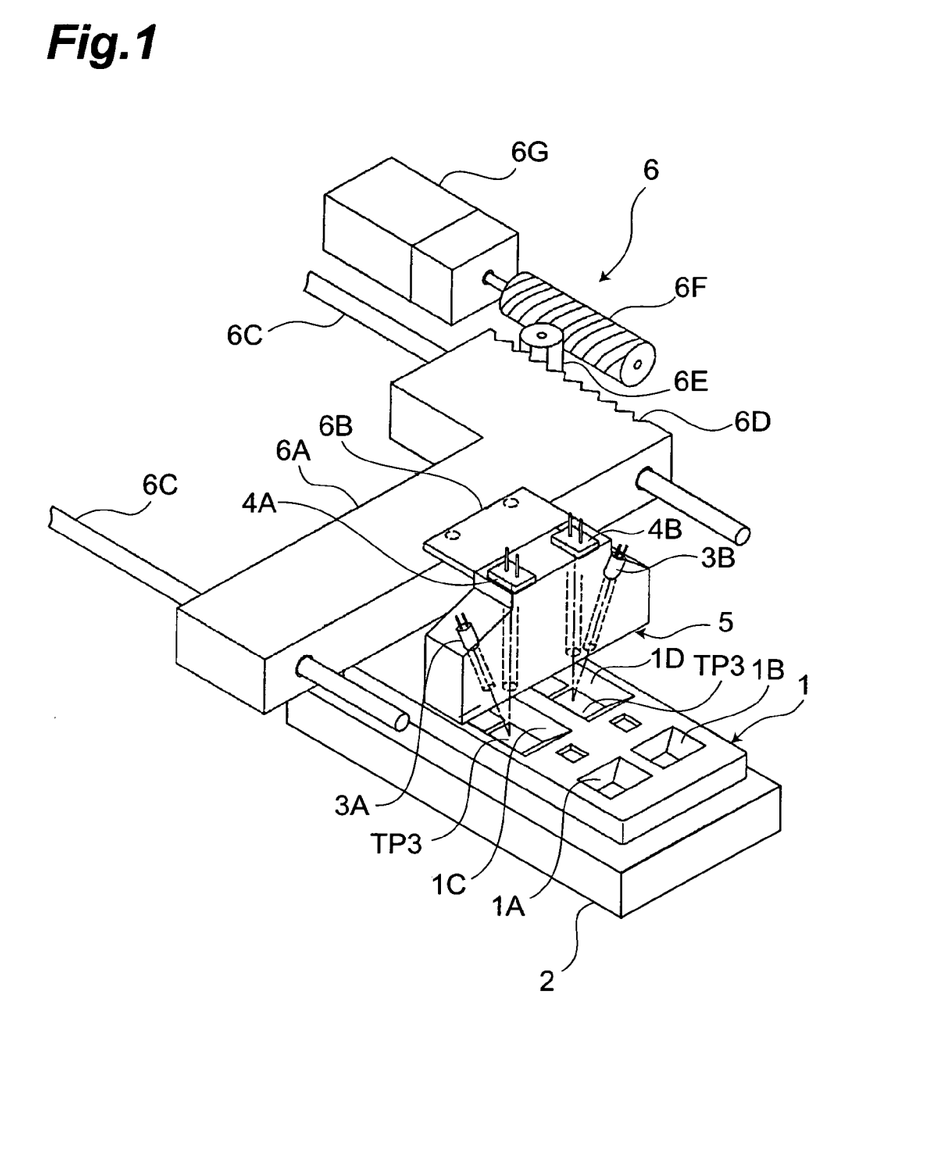
FIG. 1 is a perspective view showing a major structure of a color measuring device according to an embodiment of the present invention.
Figure 2:
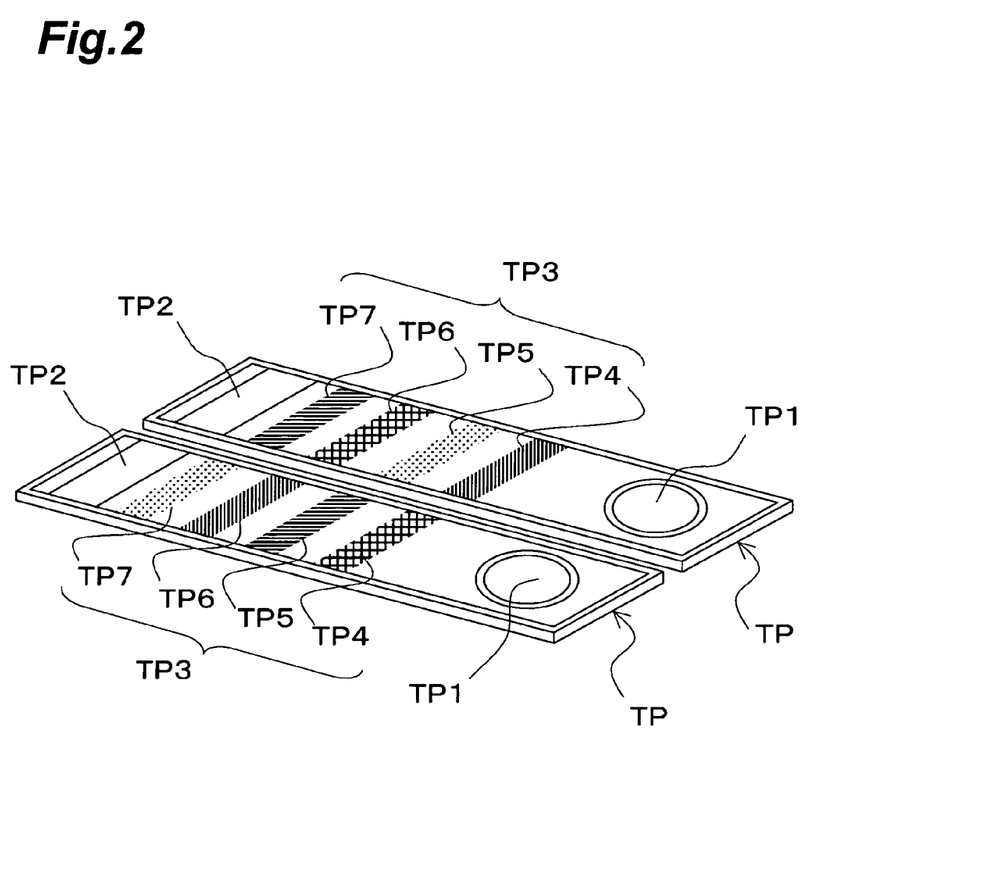
FIG. 2 is a perspective view of an immunochromatographic test strip to be measured by the color measuring device of the embodiment.
Figure 3:
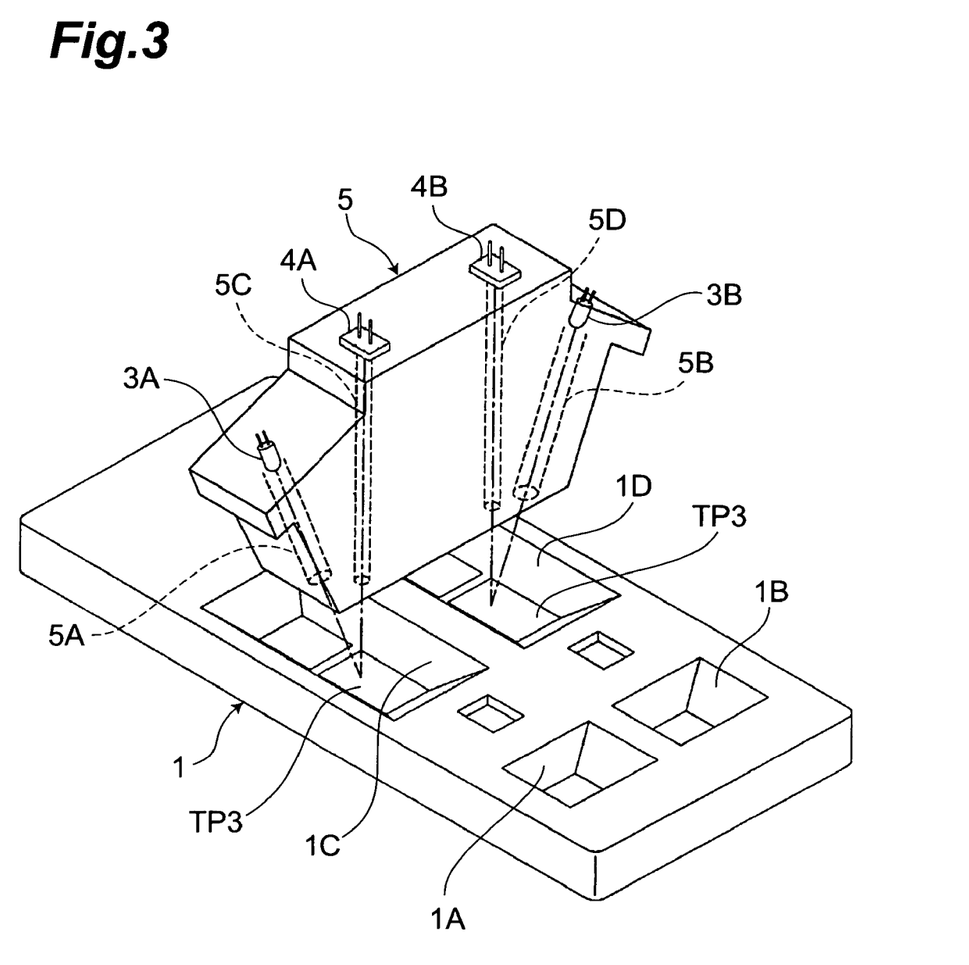
FIG. 3 is an enlarged perspective view of an optical head and a casing shown in FIG. 1.

FIG. 1 is a perspective view showing the major structure of the color measuring device according to the present embodiment. FIG. 2 is a perspective view of an immunochromatographic test strip to be measured by the color measuring device of the present embodiment. FIG. 3 is an enlarged perspective view of an optical head and a casing shown in FIG. 1.

As shown in FIG. 1, the color measuring device of the present embodiment has at least a single mount plate 2 for mounting of a specific immunochromatographic test strip (cf FIG. 2) housed in a casing 1; a pair of light emitting diodes 3A, 3B as semiconductor light emitting elements constituting a pair of irradiation optical systems; a pair of photodiodes 4A, 4B as semiconductor light receiving elements constituting a pair of reception optical systems; a single optical head 5 carrying the pair of light emitting diodes 3A, 3B and the pair of photodiodes 4A, 4B; and a scanning mechanism 6 for moving the optical head 5 relative to the mount plate 2 in a scan direction. The color measuring device of the present embodiment is, for example, a device for irradiating measurement light onto colored lines formed in color regions of an immunochromatographic test strip and for receiving reflected light thereof to measure color intensities of the colored lines.

The specific immunochromatographic test strip herein is composed of two immunochromatographic test plates TP of elongate rectangle shape, as shown in FIG. 2. At one end of each immunochromatographic test plate TP, there is provided a drop pad TP1 onto which a developing solution containing a mixture of an analyte with a dye for labeling of antigens (or antibodies) in the analyte is delivered dropwise. At the other end of each immunochromatographic test plate TP, there is provided an absorbent pad TP2 for absorbing the developing solution. A color region TP3 preliminarily coated with band-like coatings of antibodies (or antigens) to cause the antigen-antibody reaction with antigens (or antibodies) in the analyte is provided in a region (development region) in which the developing solution moves from the drop pad TP1 toward the absorbent pad TP2. Antigens (or antibodies) in the analyte bring about the antigen-antibody reaction with the bandlike coatings of antibodies (or antigens) to be trapped in the color region TP3, thereby forming a plurality of colored lines TP4-TP7 colored by the dye.

Each immunochromatographic test plate TP is comprised essentially of a nitrocellulose membrane or filter paper. Each of the drop pad TP1 and the absorbent pad TP2 is comprised of an absorbent sponge, nonwoven fabric, filter paper, or the like. The color region TP3 is preliminarily subjected to a blocking treatment by BSA or the like, in order to prevent nonspecific adsorption of protein.

The two immunochromatographic test plates TP are housed in the casing 1 in a state in which they are arranged laterally in parallel to each other and with their longer sides facing each other. A pair of left and right drop windows 1A, 1B for exposing the respective drop pads TP1 of the two immunochromatographic test plates TP are open in the upper surface at one end of the casing 1, as shown in FIG. 3. A pair of left and right measurement windows 1C, 1D for exposing the respective color regions TP3 of the two immunochromatographic test plates TP are open in the upper surface in the central part of the casing 1.

As shown in FIG. 1, the optical head 5 is formed in a laterally symmetric block shape corresponding to the lateral directions of the casing 1. The upper part of the optical head 5 is fixed through a support plate 6B to a slider block 6A forming the scanning mechanism 6, whereby the optical head 5 is supported above the casing 1.

Near the left and right ends of this optical head 5, as shown in FIG. 3, a pair of left and right irradiation paths 5A, 5B are formed through the optical head toward the color regions TP3, TP3 of the respective immunochromatographic test plates TP exposed in the pair of left and right measurement windows 1C, 1D of the casing 1. The irradiation paths 5A, 5B are obliquely inclined from the top part of the optical head 5 toward the inside in the lateral directions, and the light emitting diodes 3A, 3B for emitting the measurement light, for example, of 530 nm are buried at the upper ends of the associated irradiation paths.

In addition, a pair of left and right reception paths 5C, 5D are vertically formed through the optical head substantially perpendicularly to the casing 1, in the part between the pair of left and right irradiation paths 5A, 5B of the optical head 5, and the photodiodes 4A, 4B are buried at the upper ends of the associated reception paths. This pair of left and right reception paths 5C, 5D are positioned relative to the pair of left and right irradiation paths 5A, 5B so that each photodiode 4A, 4B can receive the measurement light emitted from the associated light emitting diode 3A, 3B through the irradiation path 5A, 5B toward the color region TP3, TP3 of the corresponding immunochromatographic test plate TP and reflected on the surface thereof As described above, the optical head 5 is equipped with plural pairs (two pairs in the present embodiment), each pair consisting of a light emitting diode 3A, 3B (irradiation optical system) for irradiating the measurement light toward the mount plate 2, and a photodiode 4A, 4B (reception optical system) for receiving light incident from the mount plate 2 side.

The scanning mechanism 6, as shown in FIG. 1, is composed of a slider block 6A, a pair of left and right guide rails 6C, 6C, a pinion 6E, a worm gear 6F, a drive motor 6G, and so on. The guide rails 6C, 6C slidably guide the slider block 6A in the longitudinal direction of the mount plate 2, i.e., in the scan direction perpendicularly traversing each colored line TP4-TP7 of the immunochromatographic test plates TP shown in FIG. 2. The pinion 6E meshes with a rack 6D formed on a side face of the slider block 6A and along the longitudinal direction of the guide rails 6C, 6C. The worm gear 6F meshes with the pinion 6E. The worm gear 6F is fixed to the drive motor 6G.

In the scanning mechanism 6, as the worm gear 6F is rotated in the normal rotation direction by the drive motor 6Q the pinion 6E is rotationally driven while reducing speed, and the slider block 6A with the rack 6D meshing with the pinion 6E is guided by the pair of left and right guide rails 6C, 6C to move in the scan direction. In consequence, the optical head 5 moves relative to the mount plate 2 in the scan direction perpendicularly traversing each colored line TP4-TP7 of the immunochromatographic test plates TP shown in FIG. 2.

The pair of light emitting diode 3A and photodiode 4A and the pair of light emitting diode 3B and photodiode 4B are juxtaposed in a direction intersecting with the scan direction (the direction perpendicular to the scan direction in the present embodiment).

Figure 4:
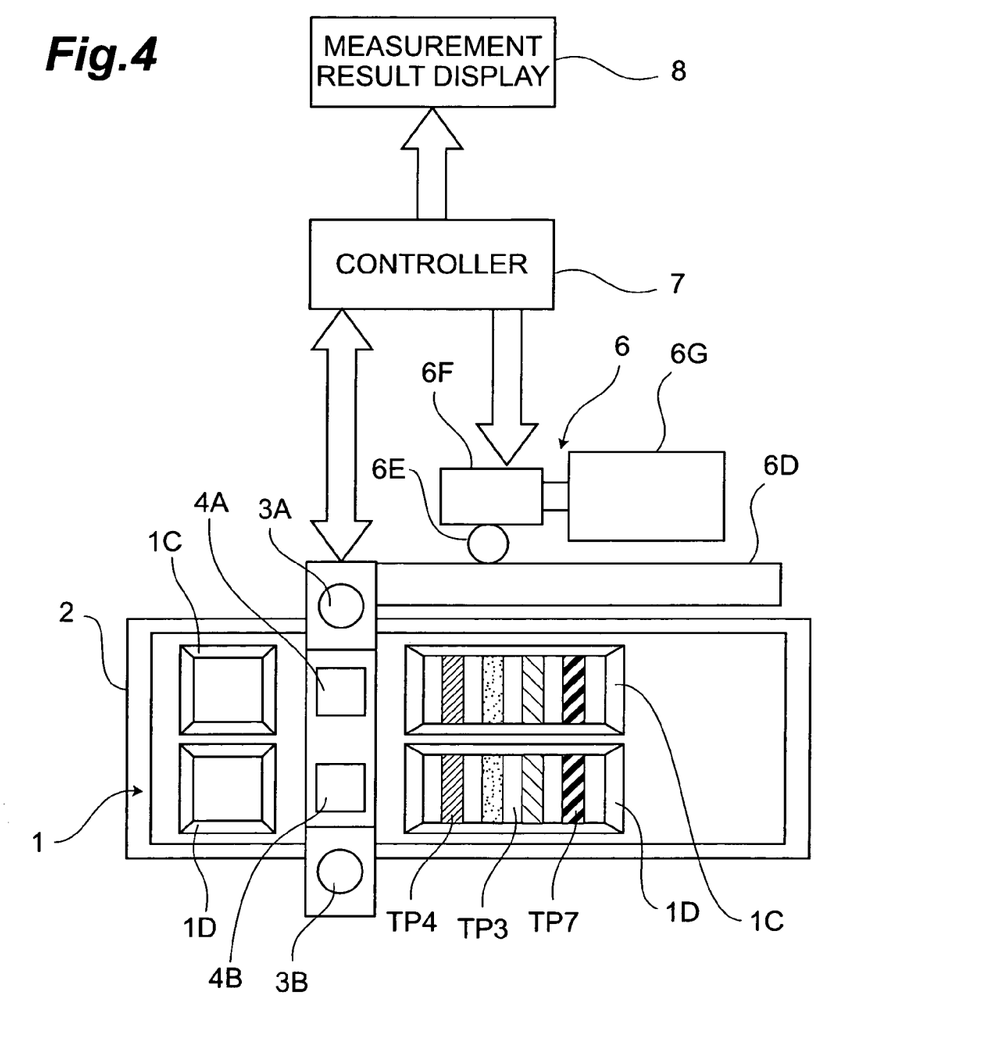
FIG. 4 is a configuration diagram of a controller and a measurement result display attached to the color measuring device according to the embodiment.

Here the color measuring device of the present embodiment, as shown in FIG. 4, is additionally provided with a controller 7 and a measurement result display 8, for control of rotation of the drive motor 6G of the scanning mechanism 6 and for control of lighting of the light emitting diodes 3A, 3B, and for processing of received signals from the photodiodes 4A, 4B and for display of the processing result.

The controller 7 controls the normal rotation, stop, and reverse rotation of the drive motor 6G of the scanning mechanism 6. In addition, the controller 7 lights up the pair of light emitting diodes 3A, 3B during the movement of the optical head 5 in the scan direction with the normal rotation of the drive motor 6Q to irradiate the measurement light onto the color regions TP3 of the respective immunochromatographic test plates TP exposed in the corresponding measurement windows 1C, 1D of the casing 1.

The controller 7 receives detection signals from the pair of photodiodes 4A, 4B having received the reflected light from the color regions TP3 of the respective immunochromatographic test plates TP with lighting of the pair of light emitting diodes 3A, 3B, and creates a reflectance pattern of the measurement light, for example, of 530 nm, based on the detection signals. Then the controller calculates an absorbance ABS of each colored line TP4-TP7 on each immunochromatographic test plate TP in accordance with an arithmetic expression of ABS=logTi/To from the reflectance pattern created. In the expression To represents the intensity of the output signal of reflected light from each colored line TP4-TP7, and Ti the intensity of the output signal of reflected light from the non-colored part.

Then the controller 7 refers to a calibration curve diagram prepared in advance, to determine a total amount (concentration) of each antigen (or antibody) included in the analyte according to the calculated absorbance ABS, and makes the measurement result display 8 display it.

The color intensities of the immunochromatographic test plates TP are measured as follows using the color measuring device of the present embodiment constructed as described above: first, the casing 1 (cf FIG. 3) housing the two immunochromatographic test plates TP, TP shown in FIG. 2 is prepared, and a developing solution containing a mixture of an analyte with a dye for labeling is delivered dropwise onto the drop pads TP1, TP1 of the immunochromatographic test plates TP, TP through the drop windows 1A, 1B of the casing 1. This results in moving the developing solution toward the absorbent pads TP2, TP2 of the immunochromatographic test plates TP, TP, whereupon the antigens (or antibodies) in the analyte bring about the antigen-antibody reaction with the bandlike coatings of antibodies (or antigens) in the color regions TP3, TP3 on the way to be trapped, thereby forming a plurality of colored lines TP4-TP7 colored with the dye.

After the preparation as described above, as shown in FIG. 1, the casing 1 housing the two immunochromatographic test plates TP, TP is mounted on the mount plate 2, and the controller 7 (cf FIG. 4) rotates the drive motor 6G in the normal rotation direction and lights up the left and right light emitting diodes 3A, 3B. In conjunction with this operation, the optical head 5 starts moving along the scan direction and the left and right light emitting diodes 3A, 3B emit the measurement light of 530 nm along the scan direction onto the respective color regions TP3, TP3 of the immunochromatographic test plates TP, TP through the measurement windows 1C, 1D of the casing 1. In concurrence therewith, the left and right photodiodes 4A, 4B receive the reflected light from the color regions TP3, TP3 of the immunochromatographic test plates TP, TP and output their detection signals to the controller 7.

Figure 5:
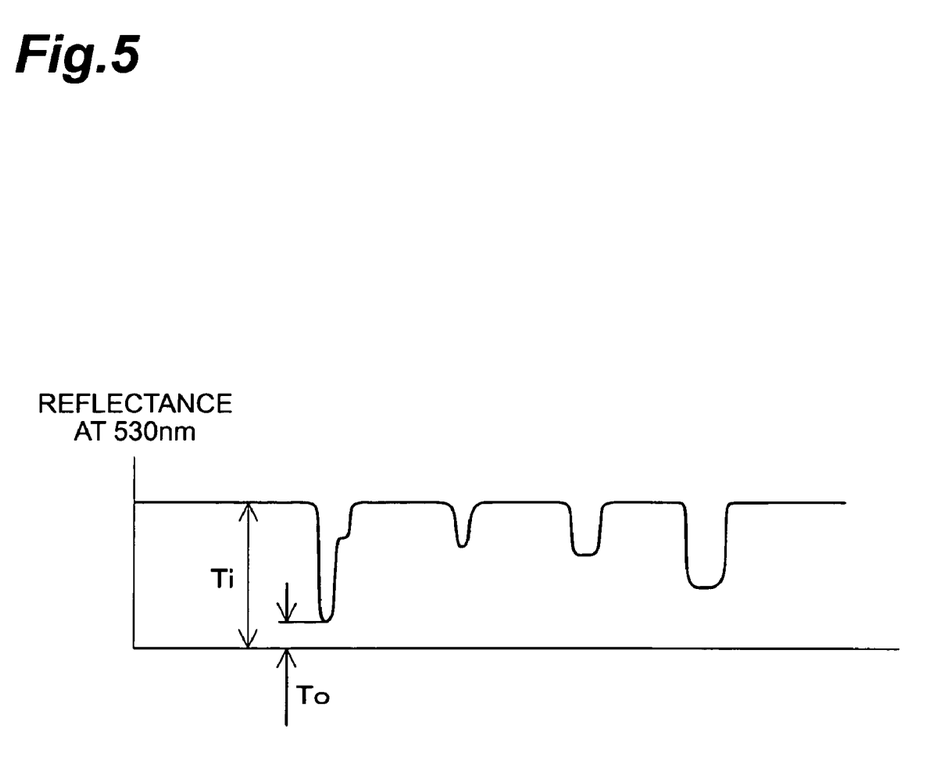
FIG. 5 is a pattern diagram of reflectance of measurement light indicating color intensities in a color region of the test strip shown in FIG. 2.

The controller 7, receiving the detection signals, creates a reflectance pattern of the measurement light of 530 nm, for example, as shown in FIG. 5, and calculates from this reflectance pattern the absorbances ABS of the colored lines TP4-TP7 colored on each immunochromatographic test plate TP, according to the arithmetic expression of ABS=logTi/To. Then the controller 7 refers to the calibration curve diagram prepared in advance, to determine the total amounts (concentrations) of the antigens (or antibodies) included in the analyte according to the calculated absorbances ABS, and makes the measurement result display 8 display the result.

In this manner, the color measuring device of the present embodiment simultaneously measures the color intensities of the respective colored lines TP4-TP7 formed in the color regions TP3, TP3 of the two immunochromatographic test plates TP, TP housed in the casing 1.

In the color measuring device of the present embodiment, the light emitting diodes 3A, 3B constituting a pair of irradiation optical systems are buried in the irradiation paths 5A, 5B of the optical head 5, and the photodiodes 4A, 4B constituting a pair of reception optical systems are buried in the reception paths 5C, 5D of the optical head 5, while being optically isolated from each other; therefore, crosstalk is prevented between the measurement light beams received by the pair of photodiodes 4A, 4B. In consequence, the color measuring device of the embodiment is able to achieve a high measurement accuracy as an accuracy of measurement of color intensities for each color region TP3 of the two immunochromatographic test plates TP.

Since the scanning mechanism 6 is configured to move the optical head 5 relative to the mount plate 2 in the scan direction, the two immunochromatographic test plates TP in the casing 1 mounted on the mount plate 2 are kept at rest without unnecessary vibration. As a result, the device is able to achieve a high measurement accuracy as an accuracy of measurement of color intensities for each color region TP3 of the two immunochromatographic test plates TP.

Furthermore, since the pair of light emitting diodes 3A, 3B and the pair of photodiodes 4A, 4B are mounted on the single optical head 5, only one system of the scanning mechanism 6 for moving the optical head 5 in the scan direction suffices, thus achieving the simple structure and the simple configuration of the control system.

Figure 6:
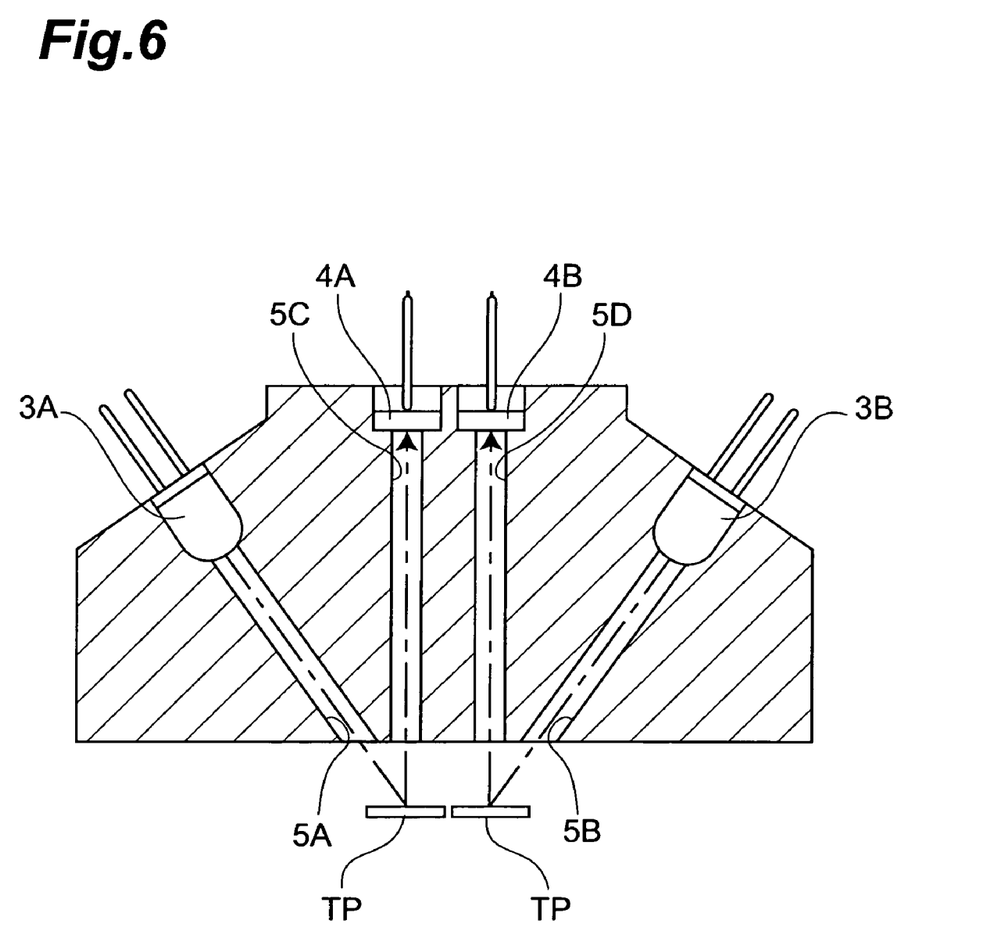
FIG. 6 is a vertical cross section showing a modification example of the optical head of the color measuring device according to the embodiment.

The present invention is by no means limited to the embodiment described above. For example, the pair of left and right reception paths 5C, 5D are arranged apart from each other in the optical head 5 shown in FIG. 3, but the spacing between them can be appropriately changed. In a case where the pair of left and right immunochromatographic test plates TP, TP are arranged close to each other in the lateral direction, as shown in FIG. 6, the pair of left and right reception paths 5C, 5D are also arranged close to each other corresponding thereto, and the pair of left and right irradiation paths 5A, 5B are also arranged close to each other at the positions of their lower ends.

The present embodiment is configured to move the optical head 5 relative to the mount plate 2 in the scan direction, but the device may also be configured to move the mount plate 2 relative to the optical head 5 in the scan direction, or to move both the mount plate 2 and the optical head 5 reciprocally in the scan direction.

The present embodiment uses the light emitting diodes 3A, 3B as semiconductor light emitting elements constituting the irradiation optical systems, but they can be replaced by other semiconductor light emitting elements such as laser diodes. The present embodiment uses the photodiodes 4A, 4B as semiconductor light receiving elements constituting the reception optical systems, but they can be replaced by other semiconductor light receiving elements such as phototransistors or CCD elements.

The color measuring device of the present invention can be applied to test strips of any kind that are test strips for measurement of color intensity, as well as the immunochromatographic test strips.

INDUSTIRIAL APPLICABILITY

The color measuring device of the present invention is applicable to color measuring devices for immunochromatographic test strips.

The invention claimed is:

1. A color measuring device for irradiating measurement light onto each colored line formed in a color region of a test strip and for receiving reflected light of the measurement light to measure a color intensity of each colored line, the device comprising:
 a single mount plate for mounting of a specific test strip in which at least two independent color regions are arranged in parallel to each other;
 a plurality of irradiation optical systems for irradiating respective beams of measurement light onto the associated color regions of the specific test strip;
 a plurality of reception optical systems for receiving respective beams of reflected light from the associated color regions;
 an optical head carrying the plurality of irradiation optical systems and reception optical systems; and
 a scanning mechanism for effecting relative movement between the mount plate and the optical head in a scan direction traversing each colored line,
 wherein the plurality of irradiation optical systems and the plurality of reception optical systems are optically isolated from each other
 wherein the scanning mechanism is arranged to move the optical head relative to the mount plate in the scan direction.

2. The color measuring device according to claim 1, wherein the plurality of irradiation optical systems and the plurality of reception optical systems are mounted on the single optical head.

3. A color measuring device for irradiating measurement light onto each colored line formed in a color region of a test strip and for receiving reflected light of the measurement light to measure a color intensity of each colored line, the device comprising:
 a single mount plate for mounting of a specific test strip in which at least two independent color regions are arranged in parallel to each other;
 a plurality of irradiation optical systems for irradiating respective beams of measurement light onto the associated color regions of the specific test strip;
 a plurality of reception optical systems for receiving respective beams of reflected light from the associated color regions;
 an optical head carrying the plurality of irradiation optical systems and reception optical systems; and
 a scanning mechanism for effecting relative movement between the mount plate and the optical head in a scan direction traversing each colored line,
 wherein the specific test strip is housed in a casing having a plurality of measurement windows for exposing at least two color regions, and a plurality of drop windows for dropwise delivery of a sample solution to effect development in each color region.

4. The color measuring device according to claim 3, wherein the plurality of irradiation optical systems and the plurality of reception optical systems are optically isolated from each other.

5. The color measuring device according to claim 3, wherein the plurality of irradiation optical systems and the plurality of reception optical systems are mounted on the single optical head.

6. The color measuring device according to claim 3, wherein the scanning mechanism is arranged to move the optical head relative to the mount plate in the scan direction.

* * * * *